US010807933B2

(12) United States Patent
Le et al.

(10) Patent No.: US 10,807,933 B2
(45) Date of Patent: *Oct. 20, 2020

(54) METHOD FOR MANUFACTURING 1,4-BIS(4-PHENOXYBENZOYL)BENZENE USING SUBSTANTIALLY NON-HYDROLYZED TEREPHTHALOYL CHLORIDE

(71) Applicant: Arkema France, Colombes (FR)

(72) Inventors: Guillaume Le, Hérouville-Saint-Clair (FR); Julien Jouanneau, Bryn Mawr, PA (US)

(73) Assignee: ARKEMA FRANCE, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/613,587

(22) PCT Filed: May 16, 2018

(86) PCT No.: PCT/EP2018/062813
§ 371 (c)(1),
(2) Date: Nov. 14, 2019

(87) PCT Pub. No.: WO2018/210971
PCT Pub. Date: Nov. 22, 2018

(65) Prior Publication Data
US 2020/0079717 A1    Mar. 12, 2020

(30) Foreign Application Priority Data
May 16, 2017   (EP) ..................... 17305562

(51) Int. Cl.
C07C 41/00    (2006.01)
C07C 45/46    (2006.01)
C08G 65/00    (2006.01)
C08L 65/00    (2006.01)
C08G 61/12    (2006.01)
C07C 45/80    (2006.01)
C08G 65/40    (2006.01)
C07C 49/84    (2006.01)

(52) U.S. Cl.
CPC .............. *C07C 45/46* (2013.01); *C07C 45/80* (2013.01); *C08G 61/127* (2013.01); *C08G 65/4012* (2013.01); *C08G 65/4093* (2013.01); *C08L 65/00* (2013.01); *C07C 49/84* (2013.01); *C08G 2261/3442* (2013.01); *C08G 2261/45* (2013.01); *C08G 2650/62* (2013.01)

(58) Field of Classification Search
CPC ......... C07C 41/36; C07C 45/46; C07C 45/79; C07C 45/80; C08G 65/4018
See application file for complete search history.

(56) References Cited

U.S. PATENT DOCUMENTS

| 4,704,448 | A  | 11/1987 | Brugel |
| 4,709,007 | A  | 11/1987 | Jansons et al. |
| 4,716,211 | A  | 12/1987 | Clendinning et al. |
| 4,794,155 | A  | 12/1988 | Woo et al. |
| 4,816,556 | A  | 3/1989  | Gay et al. |
| 4,826,947 | A  | 5/1989  | Jansons et al. |
| 4,827,041 | A  | 5/1989  | Ford et al. |
| 4,891,167 | A  | 1/1990  | Clendinning et al. |
| 4,918,237 | A  | 4/1990  | Corbin et al. |
| 4,931,530 | A  | 6/1990  | Fukuwa et al. |
| 5,137,988 | A  | 8/1992  | Matzner et al. |
| 5,258,491 | A  | 11/1993 | Agreda et al. |
| 5,734,005 | A  | 3/1998  | Daniels et al. |
| 10,344,125 | B2 | 7/2019  | Le et al. |
| 10,428,002 | B2 | 10/2019 | Jouanneau et al. |
| 10,611,715 | B2 | 4/2020  | Jouanneau et al. |
| 10,618,863 | B2 | 4/2020  | Jouanneau et al. |
| 2015/0183918 | A1 | 7/2015 | Le et al. |
| 2018/0334418 | A1 | 11/2018 | Jouanneau et al. |
| 2018/0334419 | A1 | 11/2018 | Jouanneau et al. |
| 2018/0334420 | A1 | 11/2018 | Le et al. |
| 2018/0334538 | A1 | 11/2018 | Le et al. |
| 2019/0040189 | A1 | 2/2019  | Le et al. |
| 2019/0077739 | A1 | 3/2019  | Jouanneau et al. |
| 2019/0135721 | A1 | 5/2019  | Jouanneau et al. |
| 2019/0152886 | A1 | 5/2019  | Jouanneau et al. |
| 2020/0062683 | A1 | 2/2020  | Jouanneau et al. |
| 2020/0087456 | A1 | 3/2020  | Le et al. |
| 2020/0109100 | A1 | 4/2020  | Jouanneau et al. |

FOREIGN PATENT DOCUMENTS

| EP | 0 192 260 A1 | 8/1986 |
| EP | 0 268 112 A2 | 5/1988 |
| EP | 0 298 771 A2 | 1/1989 |
| EP | 0 316 133 A2 | 5/1989 |
| EP | 0 268 112 A3 | 11/1989 |
| EP | 3 438 085 A1 | 2/2019 |
| GB | 2 287 031 A  | 9/1995 |
| IN | 193687       | 7/2004 |
| SU | 445643 A1    | 10/1974 |
| WO | 9523821 A1   | 9/1995 |

OTHER PUBLICATIONS

International Search Report (PCT/ISA/210) dated Jun. 29, 2018, by the European Patent Office as the International Searching Authority for International Application No. PCT/EP2018/062813.

(Continued)

*Primary Examiner* — Sikarl A Witherspoon
(74) *Attorney, Agent, or Firm* — Buchanan Ingersoll & Rooney P.C.

(57) ABSTRACT

A method for manufacturing 1,4-bis(4-phenoxybenzoyl)benzene, including: providing terephthaloyl chloride, diphenyl ether, a solvent and a Lewis acid, wherein the terephthaloyl chloride is of a purity grade such that, 10 minutes after introducing it at a reference concentration of 6.5 wt. % into said solvent, at a temperature of 20° C., a solution is obtained having a turbidity of less than 500 NTU; mixing the terephthaloyl chloride, the diphenyl ether and the solvent so as to make a reactant mixture; adding the Lewis acid to the reactant mixture so as to effect the reaction of the terephthaloyl chloride with the diphenyl ether; recovering a product mixture comprising a 1,4-bis(4-phenoxybenzoyl)benzene-Lewis acid complex.

16 Claims, 1 Drawing Sheet

(56) References Cited

OTHER PUBLICATIONS

Written Opinion (PCT/ISA/237) dated Jun. 29, 2018, by the European Patent Office as the International Searching Authority for International Application No. PCT/EP2018/062813.
"Database WPI Week 197630", Thomson Scientific, AN 1976 No. 30,31, AN-1976-57263X, XP002775200 , Dec. 19, 1975 , 1 page.
Mithyantha , et al. , "A process for the purification of 1,4-bis(4-phenoxybenzoyl)benzene" , Database Caplus [Online] Chemical Abstracts Service, XP002775201, Aug. 23, 2006, 1 page.
March, Jerry, "Advanced Organic Chemistry", John Wiley & Sons, XP002775202, 333.
Streitwieser, Andrew, et al. , "Introduction to Organic Chemistry" , MacMillan Publishing Co., Inc, XP002775203.
U.S. Appl. No. 16/609,648, Jouanneau et al.
U.S. Appl. No. 16/609,790, Le et al.
U.S. Appl. No. 16/613,600, Jouanneau et al.
U.S. Appl. No. 16/613,454, Jouanneau et al.
U.S. Appl. No. 16/613,456, Le et al.
Banihashemi, Ahmad, et al., "New heat stable polyethers, polyketones and polysulfones", *Macromolecular Chemistry and Physics*, vol. 200, No. 10, Oct. 1, 1999, pp. 2284-2293, WILEY-VCH Verlag GmbH, Weinheim, DE (XP055420800).
Baysec, Sebnem, et al., "Very High Solid State Photoluminescence Quantum Yields of Poly(tetraphenylethylene) Derivatives", *Macromolecular Rapid Communications*, vol. 37, No. 22, Sep. 26, 2016, pp. 1802-1806, WILEY-VCH Verlag GmbH & Co. KGaA, Weinheim, DE (XP055420789).
Brown, R. R., et al., "Solubility and Activity of Aluminum Chloride in Aqueous Hydrochloric Acid Solutions," *RI 8379—Bureau of Mines Report of Investigations/1979*, 1979, United States Department of the Interior, Reproduced by National Technical Information Service, U.S. Department of Commerce, Springfield, VA 22161, 26 pages.
Fukawa, Isaburo, et al., "Preparation of Dibenzofuran-Type Amorphous Polyetherketone by Novel Etherification Reaction", *Journal of Polymer Science: Part A: Polymer Chemistry*, Jan. 1, 1992, pp. 1977-1985, vol. 30 (XP055420842).
European Search Report in application No. EP 17305559.1, dated Nov. 9, 2017, European Patent Office, Munich, DE, 10 pages.
International Search Report and Written Opinion, issued in PCT/EP2018/062803, dated Jul. 12, 2018, European Patent Office, Rijswijk, NL, 10 pages.
European Search Report in application No. EP 17305561.7, dated Nov. 3, 2017, European Patent Office, Munich, DE,5 pages.
International Search Report and Written Opinion, issued in PCT/EP2018/062796, dated Aug. 20, 2018, European Patent Office, Rijswijk, NL,7 pages.
European Search Report in application No. EP 17305562.5, dated Dec. 6, 2017, European Patent Office, Munich, DE,10 pages.
European Search Report in application No. EP 17305581.5, dated Nov. 24, 2017, European Patent Office, Munich, DE,6 pages.
International Search Report and Written Opinion, issued in PCT/EP2018/063013, dated Jul. 24, 2018, European Patent Office, Rijswijk, NL, 8 pages.
European Search Report in application No. EP 17305582.3, dated Nov. 8, 2017, European Patent Office, Munich, DE,7 pages.
International Search Report and Written Opinion, issued in PCT/EP2018/063017, dated Jul. 4, 2018, European Patent Office, Rijswijk, NL, 9 pages.
European Search Report in application No. EP 17305583.1, dated Aug. 22, 2017, European Patent Office, Munich, DE, 8 pages.
International Search Report and Written Opinion, issued in PCT/EP2018/063014, dated Jul. 24, 2018, European Patent Office, Rijswijk, NL, 10 pages.
European Search Report in application No. EP 18306473.2, dated Apr. 18, 2019, European Patent Office, Munich, DE, 5 pages.
**Jouanneau, Julien, et al., U.S. Appl. No. 16/609,648 entitled "Method for Manufacturing 1,4-Bis(4-Phenoxybenzoyl)Benzene at an Elevated Temperature," filed in the U.S. Patent and Trademark Office Oct. 30, 2019.
**Le, Guillaume, et al., U.S. Appl. No. 16/609,790 entitled "Method for Manufacturing 1,4-Bis(4-Phenoxybenzoyl)Benzene in Supersaturation Conditions," filed in the U.S. Patent and Trademark Office Oct. 31, 2019.
**Jouanneau, Julien, et al., U.S. Appl. No. 16/613,600 entitled "Dissociation of a 1,4-Bis(4-Phenoxybenzoyl)Benzene-Lewis Acid Complex in an Aqueous Solution," filed in the U.S. Patent and Trademark Office Nov. 14, 2019.
**Jouanneau, Julien, et al., U.S. Appl. No. 16/613,454 entitled "Ripening of 1,4-Bis(4-Phenoxybenzoyl)Benzene," filed in the U.S. Patent and Trademark Office Nov. 14, 2019.
**Le, Guillaume, et al., U.S. Appl. No. 16/613,456 entitled "Purification of 1,4-Bis(4-Phenoxybenzoyl)Benzene by Centrifugal Filtration," filed in the U.S. Patent and Trademark Office Nov. 14, 2019.
Stevens, G.W., et al., "Extraction, Liquid-Liquid," *Kirk-Othmer Encyclopedia of Chemical Technology*, 2007, pp. 1-62, John Wiley & Sons, Inc., NJ, United States (published online Jun. 15, 2007).
International Search Report and Written Opinion issued in PCT/EP2019/080625, dated Jan. 20, 2020, European Patent Office, Rijswijk, NL, 7 pages.
U.S. Appl. No. 15/981,284, Julien Jouanneau, Guillaume Le and Jérôme Amstutz, filed May 16, 2018, (Cited herein as US Patent Application Publication No. 2018/0334418 A1 of Nov. 22, 2018).
U.S. Appl. No. 15/981,498, Julien Jouanneau and Guillaume Le, filed May 16, 2018, (Cited herein as US Patent Application Publication No. 2018/0334419 A1 of Nov. 22, 2018).
U.S. Appl. No. 15/982,625, Guillaume Le and Julien Jouanneau, filed May 17, 2018, (Cited herein as US Patent Application Publication No. 2018/0334420 A1 of Nov. 22, 2018).
U.S. Appl. No. 15/982,453, Julien Jouanneau, Jérôme Amstutz and Guillaume Vincent, filed May 17, 2018, (Cited herein as US Patent Application Publication No. 2019/0152886 A1 of May 23, 2019).
U.S. Appl. No. 16/186,039, Julien Jouanneau, Guillaume Le, Steven Schon, John Richardson, Guillaume Vincent, Jérôme Amstutz, filed Nov. 9, 2018, (Cited herein as US Patent Application Publication No. 2019/0077739 A1 of Mar. 14, 2019).
U.S. Appl. No. 16/609,648, Julien Jouanneau, Guillaume Le and Jérôme Amstutz, filed Oct. 30, 2019.
U.S. Appl. No. 16/609,790, Guillaume Le, Guillaume Vincent and Julien Jouanneau, filed Oct. 31, 2019.
U.S. Appl. No. 16/613,600, Julien Jouanneau and Guillaume Le, filed Nov. 14, 2019.
U.S. Appl. No. 16/613,454, Julien Jouanneau, Jérôme Amstutz and Guillaume Vincent, filed Nov. 14, 2019.
U.S. Appl. No. 16/613,456, Guillaume Le, Julien Jouanneau and Jérôme Amstutz, filed Nov. 14, 2019

METHOD FOR MANUFACTURING 1,4-BIS (4-PHENOXYBENZOYL)BENZENE USING SUBSTANTIALLY NON-HYDROLYZED TEREPHTHALOYL CHLORIDE

TECHNICAL FIELD

The present application relates to a method for manufacturing 1,4-bis(4-phenoxybenzoyl)benzene, as well as a method for manufacturing polyether ketone ketone polymers starting from said 1,4-bis(4-phenoxybenzoyl)benzene.

TECHNICAL BACKGROUND

Polyether ketone ketone (PEKK) polymers have a number of properties which make them useful for applications involving exposure to high temperature or to high mechanical or chemical stress. They are for instance useful in the aerospace industry, in off-shore drilling and in medical devices.

One known route for manufacturing polyether ketone ketone polymers relies on the use of 1,4-bis(4-phenoxybenzoyl)benzene as a starting material.

1,4-bis(4-phenoxybenzoyl)benzene can be prepared by reacting terephthaloyl chloride and diphenyl ether in the presence of a Lewis acid such as aluminum trichloride.

In document U.S. Pat. No. 4,816,556 (example 2), 1,4-bis(4-phenoxybenzoyl)benzene is prepared by dissolving terephthaloyl chloride and diphenyl ether in ortho-dichlorobenzene and adding aluminum chloride. Thereafter, cold methanol is added so as to produce a slurry which is filtered, reslurried in methanol and filtered again.

In document U.S. Pat. No. 4,826,947 (example 2), 1,4-bis(4-phenoxybenzoyl)benzene is prepared by providing a mixture of methylene chloride, methylsulfone and aluminum trichloride, adding diphenyl ether and thereafter terephthaloyl chloride. The reaction mixture is then poured into cold methanol so as to make a slurry which is then filtered.

Document WO 95/23821 (example 11) discloses providing aluminum chloride in ortho-dichlorobenzene and then adding terephthaloyl chloride and diphenyl ether. Thereafter, the reaction mixture is allowed to warm up to room temperature, stirred, and poured into a methanol concentrated HCl solution. A precipitate is formed which is subsequently filtered off.

There is still a need for a method for manufacturing 1,4-bis(4-phenoxybenzoyl)benzene with a high purity and a high yield, which can be implemented at the industrial scale in an economically realistic manner.

SUMMARY

It is a first object of the invention to provide a method for manufacturing 1,4-bis(4-phenoxybenzoyl)benzene, comprising:
  providing terephthaloyl chloride, diphenyl ether, a solvent and a Lewis acid, wherein the terephthaloyl chloride is of a purity grade such that, 10 minutes after introducing it at a reference concentration of 6.5 wt. % into said solvent, at a temperature of 20° C., a solution is obtained having a turbidity of less than 500 NTU;
  mixing the terephthaloyl chloride, the diphenyl ether and the solvent so as to make a reactant mixture;
  adding the Lewis acid to the reactant mixture so as to effect the reaction of the terephthaloyl chloride with the diphenyl ether;
  recovering a product mixture comprising a 1,4-bis(4-phenoxybenzoyl)benzene-Lewis acid complex.

In some embodiments, the terephthaloyl chloride is of a purity grade such that:
  10 minutes after introducing it at a reference concentration of 6.5 wt. % into said solvent, at a temperature of 20° C., a solution is obtained having a turbidity of less than 200 NTU, preferably of less than 50 NTU, and more preferably of less than 10 NTU;
  preferably, 10 hours after introducing it at a reference concentration of 6.5 wt. % into said solvent, at a temperature of 20° C., a solution is obtained having a turbidity of less than 500 NTU, preferably of less than 200 NTU, more preferably of less than 50 NTU and most preferably of less than 10 NTU; and
  more preferably, 24 hours after introducing it at a reference concentration of 6.5 wt. % into said solvent, at a temperature of 20° C., a solution is obtained having a turbidity of less than 500 NTU, preferably of less than 200 NTU, more preferably of less than 50 NTU and most preferably of less than 10 NTU.

In some embodiments, the terephthaloyl chloride is kept in a sealed container without contact with ambient air prior to making the reactant mixture.

In some embodiments, the diphenyl ether and solvent, in combination, contain less than 500 ppm by weight of water, advantageously less than 250 ppm by weight of water, preferably less than 150 ppm by weight of water, more preferably less than 100 ppm by weight of water, and most preferably less than 50 ppm by weight of water.

In some embodiments, the diphenyl ether and solvent, in combination, contain from 1 to 250 ppm by weight of water, preferably from 2 to 200 ppm by weight of water, more preferably from 3 to 150 ppm by weight of water, even more preferably from 4 to 100 ppm by weight of water and most preferably from 5 to 50 ppm by weight of water.

In some embodiments, the method comprises a step of drying the solvent or of drying the solvent combined with the diphenyl ether prior to adding the terephthaloyl chloride to the solvent, preferably by distillation or by contacting with a molecular sieve or with a dehydrating agent.

In some embodiments, the 1,4-bis(4-phenoxybenzoyl)benzene-Lewis acid complex is dissolved in the solvent at a 1,4-bis(4-phenoxybenzoyl)benzene weight concentration in the solvent which is higher than the saturation limit of the 1,4-bis(4-phenoxybenzoyl)benzene-Lewis acid complex during at least part of the reaction of the terephthaloyl chloride with the diphenyl ether.

In some embodiments, the 1,4-bis(4-phenoxybenzoyl)benzene-Lewis acid complex is dissolved in the solvent at a 1,4-bis(4-phenoxybenzoyl)benzene weight concentration which is higher by at least 5%, preferably by at least 10%, more preferably by at least 20%, than the saturation limit of the 1,4-bis(4-phenoxybenzoyl)benzene-Lewis acid complex, during part of the reaction of the terephthaloyl chloride with the diphenyl ether.

In some embodiments, the 1,4-bis(4-phenoxybenzoyl)benzene-Lewis acid complex is dissolved in the solvent at a 1,4-bis(4-phenoxybenzoyl)benzene weight concentration of more than 5 wt. %, preferably more than 10 wt. %, more preferably more than 15 wt. %, and most preferably more than 30 wt. %, during part of the reaction of the terephthaloyl chloride with the diphenyl ether.

In some embodiments, the 1,4-bis(4-phenoxybenzoyl)benzene-Lewis acid complex is dissolved in the solvent during at least 75%, preferably at least 90%, more preferably at least 95% of the duration of the reaction of the terephthaloyl chloride with the diphenyl ether, and most preferably during the totality of the reaction of the terephthaloyl chloride with the diphenyl ether.

In some embodiments, the 1,4-bis(4-phenoxybenzoyl)benzene-Lewis acid complex is dissolved in the solvent when an amount of 1,4-bis(4-phenoxybenzoyl)benzene of 75 mol. %, relative to the initial amount of terephthaloyl chloride, is present in the reactant mixture; preferably the 1,4-bis(4-phenoxybenzoyl)benzene-Lewis acid complex is dissolved in the solvent when an amount of 1,4-bis(4-phenoxybenzoyl)benzene of 80 mol. %, relative to the initial amount of terephthaloyl chloride, is present in the reactant mixture; more preferably the 1,4-bis(4-phenoxybenzoyl)benzene-Lewis acid complex is dissolved in the solvent when an amount of 1,4-bis(4-phenoxybenzoyl)benzene of 85 mol. %, relative to the initial amount of terephthaloyl chloride, is present in the reactant mixture; and most preferably, the 1,4-bis(4-phenoxybenzoyl)benzene-Lewis acid complex is dissolved in the solvent when an amount of 1,4-bis(4-phenoxybenzoyl)benzene of 90 mol. %, relative to the initial amount of terephthaloyl chloride, is present in the reactant mixture.

In some embodiments, the Lewis acid is aluminum trichloride.

In some embodiments, the solvent is a separate solvent and preferably may be ortho-dichlorobenzene. As an alternative, the solvent may be diphenyl ether.

In some embodiments, the method comprises the additional steps of:
- mixing the product mixture with a protic solvent so as to provide a product slurry;
- separating 1,4-bis(4-phenoxybenzoyl)benzene from the product slurry, preferably by filtration and optionally washing.

The invention also relates to a method of making a polyether ketone ketone polymer, comprising:
- manufacturing 1,4-bis(4-phenoxybenzoyl)benzene according to the method described above;
- reacting said 1,4-bis(4-phenoxybenzoyl)benzene with at least one difunctional aromatic acyl chloride.

Independently from the above, the invention additionally provides the following items:

Item 1. A method for manufacturing 1,4-bis(4-phenoxybenzoyl)benzene, comprising:
- providing terephthaloyl chloride, diphenyl ether, a solvent and a Lewis acid, wherein the diphenyl ether and solvent, in combination, contain less than 500 ppm by weight of water;
- mixing the terephthaloyl chloride, the diphenyl ether and the solvent so as to provide a reactant mixture;
- adding the Lewis acid to the reactant mixture so as to effect the reaction of the terephthaloyl chloride with the diphenyl ether;
- recovering a product mixture comprising a 1,4-bis(4-phenoxybenzoyl)benzene-Lewis acid complex.

Item 2. The method of item 1, wherein the diphenyl ether and solvent, in combination, contain less than 250 ppm by weight of water, preferably less than 150 ppm by weight of water, more preferably less than 100 ppm by weight of water, and most preferably less than 50 ppm by weight of water.

Item 3. The method of item 1 or item 2, wherein the terephthaloyl chloride is of a purity grade such that, 10 minutes after introducing it at a reference concentration of 6.5 wt. % into said solvent, at a temperature of 20° C., a solution is obtained having a turbidity of less than 500 NTU.

Item 4. The method of any of items 1 to 3, wherein the terephthaloyl chloride is of a purity grade such that:
- 10 minutes after introducing it at a reference concentration of 6.5 wt. % into said solvent, at a temperature of 20° C., a solution is obtained having a turbidity of less than 200 NTU, preferably of less than 50 NTU, and more preferably of less than 10 NTU;
- preferably, 10 hours after introducing it at a reference concentration of 6.5 wt. % into said solvent, at a temperature of 20° C., a solution is obtained having a turbidity of less than 500 NTU, preferably of less than 200 NTU, more preferably of less than 50 NTU and most preferably of less than 10 NTU; and
- more preferably, 24 hours after introducing it at a reference concentration of 6.5 wt. % into said solvent, at a temperature of 20° C., a solution is obtained having a turbidity of less than 500 NTU, preferably of less than 200 NTU, more preferably of less than 50 NTU and most preferably of less than 10 NTU.

Item 5. The method of any of items 1 to 4, wherein the diphenyl ether and solvent, in combination, contain from 1 to 250 ppm of water, preferably from 2 to 200 ppm by weight of water, more preferably from 3 to 150 ppm by weight of water, even more preferably from 4 to 100 ppm by weight of water and most preferably from 5 to 50 ppm by weight of water.

Item 6. The method of any of items 1 to 5, comprising a step of drying the solvent or of drying the solvent combined with the diphenyl ether prior to adding the terephthaloyl chloride to the solvent, preferably by distillation or by contacting with a molecular sieve or with a dehydrating agent.

Item 7. The method of any of items 1 to 6, wherein the terephthaloyl chloride is kept in a sealed container without contact with ambient air prior to making the reactant mixture.

Item 8. The method of any of items 1 to 7, wherein the 1,4-bis(4-phenoxybenzoyl)benzene-Lewis acid complex is dissolved in the solvent at a 1,4-bis(4-phenoxybenzoyl)benzene weight concentration in the solvent which is higher than the saturation limit of the 1,4-bis(4-phenoxybenzoyl)benzene-Lewis acid complex during at least part of the reaction of the terephthaloyl chloride with the diphenyl ether.

Item 9. The method of any of items 1 to 8, wherein the 1,4-bis(4-phenoxybenzoyl)benzene-Lewis acid complex is dissolved in the solvent at a 1,4-bis(4-phenoxybenzoyl)benzene weight concentration which is higher by at least 5%, preferably by at least 10%, more preferably by at least 20%, than the saturation limit of the 1,4-bis(4-phenoxybenzoyl)benzene-Lewis acid complex, during part of the reaction of the terephthaloyl chloride with the diphenyl ether.

Item 10. The method of any of items 1 to 9, wherein the 1,4-bis(4-phenoxybenzoyl)benzene-Lewis acid complex is dissolved in the solvent at a 1,4-bis(4-phenoxybenzoyl)benzene weight concentration of more than 5 wt. %, preferably more than 10 wt. %, more preferably more than 15 wt. %, and most preferably more than 30 wt. %, during part of the reaction of the terephthaloyl chloride with the diphenyl ether.

Item 11. The method of any one of any of items 1 to 10, wherein the 1,4-bis(4-phenoxybenzoyl)benzene-Lewis acid complex is dissolved in the solvent during at least 75%, preferably at least 90%, more preferably at least 95% of the duration of the reaction of the terephthaloyl chloride with the diphenyl ether, and most preferably during the totality of the reaction of the terephthaloyl chloride with the diphenyl ether.

Item 12. The method of any one of any of items 1 to 11, wherein the 1,4-bis(4-phenoxybenzoyl)benzene-Lewis acid complex is dissolved in the solvent when an amount of 1,4-bis(4-phenoxybenzoyl)benzene of 75 mol. %, relative to the initial amount of terephthaloyl chloride, is present in the reactant mixture; preferably the 1,4-bis(4-phenoxybenzoyl)benzene-Lewis acid complex is dissolved in the solvent when an amount of 1,4-bis(4-phenoxybenzoyl)benzene of 80 mol. %, relative to the initial amount of terephthaloyl chloride, is present in the reactant mixture; more preferably the 1,4-bis(4-phenoxybenzoyl)benzene-Lewis acid complex is dissolved in the solvent when an amount of 1,4-bis(4-phenoxybenzoyl)benzene of 85 mol. %, relative to the initial amount of terephthaloyl chloride, is present in the reactant mixture; and most preferably, the 1,4-bis(4-phenoxybenzoyl)benzene-Lewis acid complex is dissolved in the solvent when an amount of 1,4-bis(4-phenoxybenzoyl)benzene of 90 mol. %, relative to the initial amount of terephthaloyl chloride, is present in the reactant mixture.

Item 13. The method of any of items 1 to 12, wherein the Lewis acid is aluminum trichloride.

Item 14. The method of any of items 1 to 13, wherein the solvent is ortho-dichlorobenzene.

Item 15. The method of any of items 1 to 14, comprising the additional steps of:
mixing the product mixture with a protic solvent so as to provide a product slurry;
separating 1,4-bis(4-phenoxybenzoyl)benzene from the product slurry, preferably by filtration and optionally washing.

Item 16. A method of making a polyether ketone ketone polymer, comprising:
manufacturing 1,4-bis(4-phenoxybenzoyl)benzene according to the method of any of items 1 to 15;
reacting said 1,4-bis(4-phenoxybenzoyl)benzene with at least one difunctional aromatic acyl chloride.

The present invention provides a method for manufacturing 1,4-bis(4-phenoxybenzoyl)benzene with a high purity and a high yield. This method can be implemented at the industrial scale.

In a first aspect, it has been found that the quality of the terephthaloyl chloride used as a starting material is critical for achieving high purity and high yield in the manufacture of 1,4-bis(4-phenoxybenzoyl)benzene. In particular, one acyl chloride group or both acyl chloride groups in terephthaloyl chloride may react with water potentially present in the material's environment. The presence of hydrolyzed forms of terephthaloyl chloride is undesirable for two reasons: first, the hydrolyzed portion of terephthaloyl chloride will not lead to the production of 1,4-bis(4-phenoxybenzoyl)benzene; second, the hydrolyzed portion of terephthaloyl chloride tends to be insoluble in the solvent used for the reaction.

It is desirable to maintain the 1,4-bis(4-phenoxybenzoyl)benzene-Lewis acid complex which is produced during the reaction as a supersaturated solution during at least part of the reaction, in order to achieve a high yield of 1,4-bis(4-phenoxybenzoyl)benzene and a low level of by-product impurities such as 4-(4-phenoxybenzoyl)benzoyl chloride and its corresponding carboxylic acid and ester forms. In this context, and without wishing to be bound by any theory, it is believed that the hydrolyzed portion of terephthaloyl chloride in the starting material may act as a nucleating agent for the precipitation of the 1,4-bis(4-phenoxybenzoyl)benzene-Lewis acid complex and thus prevent said complex from being maintained as a supersaturated solution during the reaction.

In a second aspect, it has been found that the presence of even relatively low amounts of water during the reaction of terephthaloyl chloride and diphenyl ether may lead to a relatively large decrease in reaction yield and/or in the purity of final product. The presence of water in the reactant mixture may indeed lead to the hydrolysis of the terephthaloyl chloride starting material within the reactant mixture, which is undesirable for the reasons already set forth above. In addition, water droplets may also act as a nucleating agent of their own.

By maintaining the amount of water in the solvent and diphenyl ether below a desired threshold, the yield of 1,4-bis(4-phenoxybenzoyl)benzene may be increased, and the level of by-product impurities such as 4-(4-phenoxybenzoyl)benzoyl chloride and its corresponding carboxylic acid and ester forms may remain low.

DESCRIPTION OF EMBODIMENTS

Figure 1:
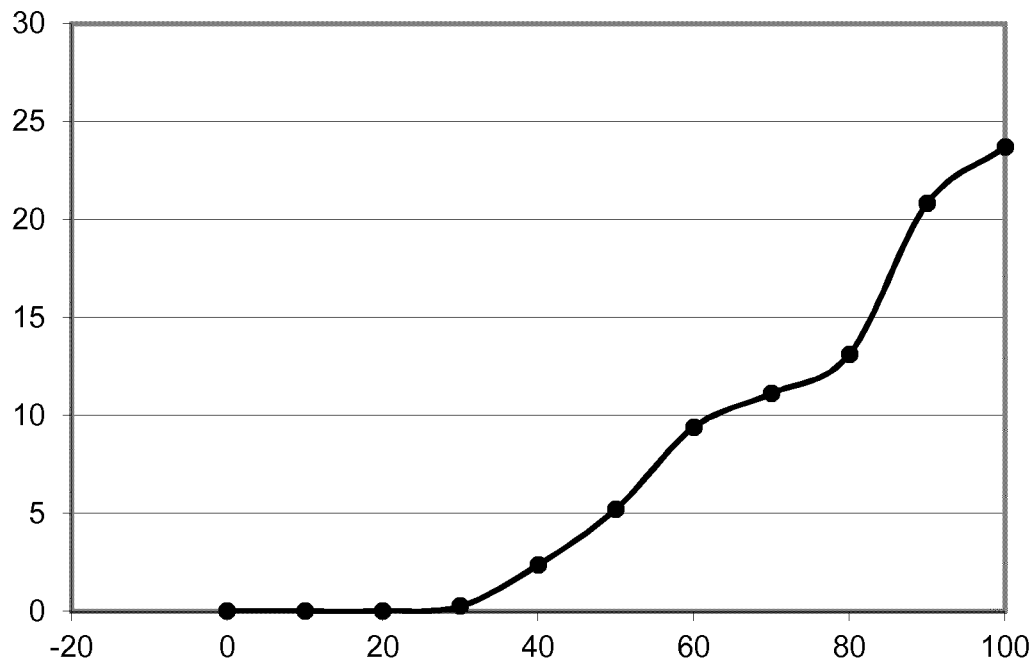
FIG. 1 shows the saturation limit of the 1,4-bis(4-phenoxybenzoyl)benzene-Lewis acid complex in ortho-dichlorobenzene, as a function of temperature. Temperature in ° C. is provided on the X axis. The weight concentration of 1,4-bis(4-phenoxybenzoyl)benzene at saturation is provided in the Y axis. The Lewis acid-to-1,4-bis(4-phenoxybenzoyl)benzene molar ratio is 4.05. The Lewis acid is aluminum trichloride.

The invention will now be described in more detail without limitation in the following description.

1,4-bis(4-phenoxybenzoyl)benzene is the compound of formula I:

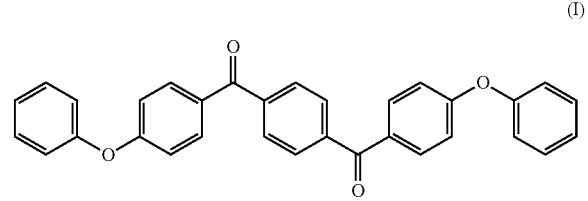 [SMILES: O=C(c1ccc(Oc2ccccc2)cc1)c1ccc(C(=O)c2ccc(Oc3ccccc3)cc2)cc1]

(I)

It may be made by reacting terephthaloyl chloride of formula II:

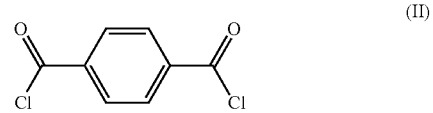

(II)

with diphenyl ether of formula III:

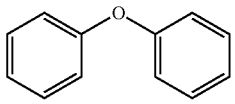

(III)

in a separate solvent, and in the presence of a Lewis acid, acting as a Friedel-Crafts catalyst. This is hereafter called "the reaction step".

The reaction results in the production of the compound of formula I which is predominantly in the form of a complex with the Lewis acid.

It is believed that the reaction comprises two stages. In the first stage, one molecule of formula II reacts with one molecule of formula III to form the following intermediate of formula IV (4-(4-phenoxybenzoyl)benzoyl chloride) which is called an "active intermediate":

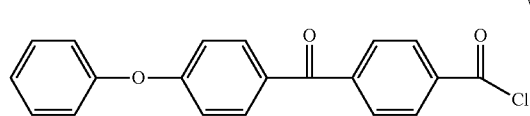

(IV)

Then one molecule of the active intermediate of formula IV reacts with another molecule of formula III to form the desired product of formula I.

During the reaction, the following 4-(4-phenoxybenzoyl) benzoic acid of formula IVa can also be produced to some extent (notably from the active intermediate of formula IV):

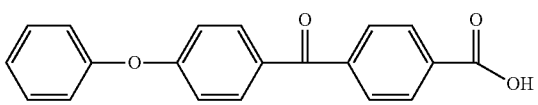

(IVa)

The corresponding 4-(4-phenoxybenzoyl)benzoic acid ester can be formed either directly from the acyl chloride of formula IV or from the carboxylic acid of formula IVa. The acid form and/or the ester form of the intermediate can be formed during the reaction but they can also primarily be formed from the remaining active intermediate during subsequent workup (such as when the product mixture is mixed with a protic solvent, as described below).

The 4-(4-phenoxybenzoyl)benzoic acid and 4-(4-phenoxybenzoyl)benzoic acid ester are inactive and therefore remain as impurities in the product mixture.

The other main impurities produced by the reaction are xanthydrol moiety-containing molecules.

The solvent is preferably a non-protic solvent, which can in particular be selected from methylene chloride, carbon disulfide, ortho-dichlorobenzene, meta-dichlorobenzene, para-dichlorobenzene, 1,2,4-trichlorobenzene, 1,2,3-trichlorobenzene, ortho-difluorobenzene, 1,2-dichloroethane, 1,1,2,2-tetrachloroethane, tetrachloroethylene, dichloromethane, nitrobenzene and mixtures thereof.

Ortho-dichlorobenzene is the most preferred solvent.

Lewis acids which may be used include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. Aluminum trichloride, boron trichloride, aluminum tribromide, titanium tetrachloride, antimony pentachloride, ferric chloride, gallium trichloride, and molybdenum pentachloride are preferred. Aluminum trichloride is particularly preferred.

According to one aspect of the invention, the compound of formula II used as a starting material is provided with a high purity grade. Hydrolyzed forms of the compound of formula II are difficult to analyze and quantify in the starting material. It has been found that one practical method to ensure that the compound of formula II has the requisite purity is to dissolve it in the solvent intended for the reaction, and to analyze its turbidity. It has been found that a high turbidity value in this test (which is indicative of a significant amount of insoluble contaminants within the starting material) results in a poor yield and a high amount of undesirable by-products in the manufacture of the compound of formula I.

Accordingly, the compound of formula II is preferably of a purity grade such that, 10 minutes after introducing it at a reference concentration of 6.5 wt. % in the solvent, at a temperature of 20° C., a solution is obtained having a turbidity of less than 500 NTU. Turbidity values are provided relative to a sample of solvent without compound of formula II.

The turbidity may be assessed by introducing 1580 mg of terephthaloyl chloride into 22.6 g of solvent in a 50 mL flask, and by agitating the mixture with a magnetic stirrer, under nitrogen atmosphere. After 10 minutes, the turbidity of the mixture may be measured on a 20 mL sample with a Hach Lange Turbidimeter, using the same solvent as a blank sample.

Preferably, the turbidity is less than 200 NTU, more preferably less than 50 NTU and most preferably less than 10 NTU.

A more stringent test consists in waiting for 10 hours, or even for 24 hours, between the introduction of the compound of formula II into the solvent and the turbidity measurement. Preferably, turbidity values of less than 500 NTU, preferably less than 200 NTU, more preferably less than 50 NTU and most preferably less than 10 NTU are obtained in this more stringent test.

In some variations, a second turbidity value may be obtained with a sample of solvent of so-called anhydrous grade; which is stored on a molecular sieve. Preferably, the anhydrous grade of solvent is characterized by a water weight content of less than 50 ppm, preferably of less than 30 ppm. In embodiments, the second, anhydrous turbidity value may be less than 500 NTU, preferably less than 200 NTU, more preferably less than 50 NTU and most preferably less than 10 NTU.

In other variations, the turbidity values indicated herein are obtained using a sample of the batch of solvent which is used for the reaction itself. This is particularly advantageous for the turbidity measurements conducted 10 hours or 24 hours after the introduction of the compound into the solvent, since the measurement is then representative of the actual quality of the compound in the reaction conditions, depending also on the quality of the solvent.

A number of steps can be taken in order to ensure that the compound of formula II is of a satisfactory purity grade. In particular, the compound should substantially not be in contact with water at any time before the reaction. It can thus be advantageous to keep this material in a sealed container without contact with ambient air. Keeping the material in a nitrogen atmosphere may in particular be useful.

As a sealed container, use may in particular be made of a container having walls and a lid having a moisture vapor transmission rate of not more than 0.1 g/m² 0.24 h at a relative humidity of 90% and a temperature of 37.8° C.

The container walls may be for instance made of polyethylene, such as high-density polyethylene.

The container walls may preferably have a thickness of at least 0.5 mm, more preferably at least 1 mm.

According to another aspect of the invention, the solvent and the compound of formula III used for the reaction have a low water content.

Accordingly, the solvent used for the reaction preferably contains less than 500 ppm by weight of water, advantageously less than 250 ppm by weight of water, preferably less than 150 ppm by weight of water, more preferably less than 100 ppm by weight of water, and most preferably less than 50 ppm by weight of water. In preferred variations, the above weight ranges also apply in a similar manner to the compound of formula III and the solvent in combination.

Possible weight ranges of water content in the solvent are: from 1 to 5 ppm; or from 5 to 10 ppm; or from 10 to 20 ppm; or from 20 to 30 ppm; or from 30 to 40 ppm; or from 40 to 50 ppm; or from 50 to 75 ppm; or from 75 to 100 ppm; or from 100 to 150 ppm; or from 150 to 200 ppm; or from 200 to 250 ppm; or from 250 to 300 ppm; or from 300 to 350 ppm; or from 350 to 400 ppm; or from 400 to 500 ppm. Ranges of from 1 to 250 ppm, or from 2 to 200 ppm, or from 3 to 150 ppm, or from 4 to 100 ppm, or from 5 to 50 ppm are particularly preferred. In preferred variations, the above weight ranges also apply in a similar manner to the compound of formula III and the solvent in combination.

A number of steps can be taken in order to ensure that the compound of formula III and/or the solvent do not contain an excessive amount of water. In particular it is desirable to keep these materials in sealed containers without contact with ambient air. Keeping the materials in a nitrogen atmosphere may in particular be useful.

In some variations, the method of the invention comprises a preliminary step of drying, i.e., reducing the water content, of the solvent, or of the solvent combined with the compound of formula III, before adding the compound of formula II to the solvent to form the reactant mixture. This step may be performed, e.g., by distillation or by contacting with a molecular sieve or with a dehydrating agent.

By way of example, the weight proportion of water in the solvent, or in the solvent combined with the compound of formula III, may be reduced owing to the drying step from an initial value of 50 to 300 ppm to a final value of less than 100 ppm, preferably less than 50 ppm, more preferably less than 30 ppm.

The Lewis acid used in the method of the invention is preferably of a purity grade such that it comprises less than 0.1 wt. % insoluble matter, and more preferably less than 0.05 wt. % insoluble matter, as measured by gravimetry, when introduced into the solvent at a concentration of 5 wt. % and substantially dissolved under agitation.

The reaction between the compounds of formulas II and III to make the compound of formula I may be performed in a reactor. The reactor can be for instance a glass reactor, a glass-lined reactor or a stainless-steel reactor.

Preferably, the reaction may be performed under a substantially water-free atmosphere, such as a nitrogen atmosphere.

According to some variations, the materials introduced into the reactor in the method of the invention consist essentially, or consist, of the compounds of formulas II and III, the solvent and the Lewis acid.

According to other variations, the materials introduced into the reactor in the method of the invention additionally comprise one or more additives for increasing the solubility of Lewis acid complexes. These additives may notably be selected from Lewis bases such as diphenylsulfone, carboxylic acids, ethers and inorganic salts such as LiCl, NaCl, KCl, $CaCl_2$ and $MgCl_2$, as well as mixtures thereof.

According to the invention, an initial reactant mixture comprising (and preferably consisting of) terephthaloyl chloride and diphenyl ether in a solvent is provided. The reactant mixture can be made by mixing the three components together, in any order. By way of example, the solvent can be introduced first into the reactor, and then the two reactants can be added to the reactor.

In some variations, the solvent is introduced first into the reactor, then the compound of formula III, and then the compound of formula II.

In other variations, a mixture of solvent and compound of formula III is introduced first into the reactor, and then the compound of formula II.

As a second step, the Lewis acid is added to the reactant mixture. Preferably, the Lewis acid is added as a solid. Alternatively, it can also be added as a suspension or a solution, preferably in the abovementioned solvent.

In some variations, the Lewis acid is added in a particulate form, such as in the form of granules (having, e.g., a Dv80 of more than 1 mm) or in the form of a powder (having, e.g., a Dv80 of less than 1 mm, and preferably a Dv50 of less than 0.5 mm). Dv80 and Dv50 are respectively the particle sizes at the $80^{th}$ and $50^{th}$ percentiles (in volume) of the cumulative size distribution of the Lewis acid particles. These parameters may be determined by sieving.

In some particular embodiments, the weight concentrations and weight ratios of the reactants and of the catalyst are as follows:

the concentration of terephthaloyl chloride (relative to the sum of solvent, terephthaloyl chloride, diphenyl ether and Lewis acid introduced into the reactor) is from 3 to 12%, preferably from 5 to 10%;

the concentration of diphenyl ether (relative to the sum of solvent, terephthaloyl chloride, diphenyl ether and Lewis acid introduced into the reactor) is from 5 to 35%, preferably from 12 to 25%;

the concentration of Lewis acid (relative to the sum of solvent, terephthaloyl chloride, diphenyl ether and Lewis acid introduced into the reactor) is from 4 to 30%, preferably from 10 to 25%;

the weight ratio of terephthaloyl chloride to diphenyl ether introduced into the reactor is from 0.2 to 0.6, preferably from 0.3 to 0.5;

the weight ratio of Lewis acid to terephthaloyl chloride plus diphenyl ether introduced into the reactor is from 0.2 to 0.9, preferably from 0.3 to 0.7.

The addition of the Lewis acid is preferably performed progressively, over a period of time which can advantageously range from 5 to 600 minutes, preferably from 30 to 300 minutes.

The addition can be performed continuously or with one or more interruptions. If it is performed continuously, it can be conducted at a constant rate of addition. Alternatively, the rate of addition can vary over time.

The reactant mixture may preferably be agitated during at least part of the reaction step. Thus, the reactor is preferably provided with an agitation device such as a mechanical stirrer (which may, e.g., comprise one or more impellers) or a recirculation loop with a pump.

Preferably, the reactant mixture may be agitated owing to the agitation device during the addition of the Lewis acid.

Once the addition of the Lewis acid to the reactant mixture is complete, the reaction step may optionally comprise a step of maintaining the reactant mixture, preferably under agitation, for a certain time, in order to complete the reaction to the desired degree. Preferably, the mixture is maintained from 0 to 600 min, more preferably from 5 to 180 min.

Once the reaction is completed to the desired degree, the reactant mixture becomes designated as a product mixture.

The end of the reaction step corresponds to the beginning of the next step in the method, which is usually a purification step, as described in more detail below.

During the reaction step, 1,4-bis(4-phenoxybenzoyl)benzene-Lewis acid complex is initially produced as a dissolved species, the concentration of which progressively increases.

In preferred embodiments, at some point of time during the reaction step, the concentration of the 1,4-bis(4-phenoxybenzoyl)benzene-Lewis acid complex exceeds the saturation limit of the 1,4-bis(4-phenoxybenzoyl)benzene-Lewis acid complex. In other terms, in these embodiments, the 1,4-bis(4-phenoxybenzoyl)benzene-Lewis acid complex is maintained in a supersaturated state during at least part of the step of reacting terephthaloyl chloride with diphenyl ether.

This saturation limit depends on the conditions of the reactant mixture in real time and may vary during the reaction step. In particular, it depends on the temperature of the reactant mixture, the nature of the solvent and the amount of Lewis-acid.

The 1,4-bis(4-phenoxybenzoyl)benzene-Lewis acid complex is said to be in a supersaturated state when it is dissolved in the reactant mixture at a concentration exceeding the saturation limit. The supersaturated state is a metastable state. Therefore, the 1,4-bis(4-phenoxybenzoyl)benzene-Lewis acid complex in a supersaturated state is able to suddenly precipitate if a nucleating agent (e.g., solid particles) is present in the reactant mixture.

By way of convention, in the present application the concentration of the 1,4-bis(4-phenoxybenzoyl)benzene-Lewis acid complex is indicated by the weight concentration of 1,4-bis(4-phenoxybenzoyl)benzene in the solvent. The same applies to the saturation limit.

The saturation limit can be determined using the following model experiment: predetermined quantities of 1,4-bis(4-phenoxybenzoyl)benzene and Lewis acid are added to a given solvent contained in a glass tube. The contents of the glass tube are agitated by magnetic stirring. The temperature of the mixture within the tube is controlled by placing the tube in a thermofluid. The initial temperature is such that the 1,4-bis(4-phenoxybenzoyl)benzene-Lewis acid complex is initially present as a suspension in the solvent. Then the temperature is gradually increased until the 1,4-bis(4-phenoxybenzoyl)benzene-Lewis acid complex gets fully solubilized in the solvent. At this particular temperature, the saturation limit is equal to the weight concentration of 1,4-bis(4-phenoxybenzoyl)benzene in the mixture. The experiment can be repeated a number of times using another weight concentration of 1,4-bis(4-phenoxybenzoyl)benzene and the same weight ratio of Lewis acid with respect to 1,4-bis(4-phenoxybenzoyl)benzene, so that a temperature/saturation curve can be finally obtained for a given solvent and a given weight ratio of Lewis acid to 1,4-bis(4-phenoxybenzoyl)benzene.

FIG. 1 shows by way of illustration the temperature/saturation curve obtained as described above in ortho-dichlorobenzene as a solvent, with a Lewis acid-to-1,4-bis(4-phenoxybenzoyl)benzene molar ratio of 4.05. If the 1,4-bis(4-phenoxybenzoyl)benzene-Lewis acid complex is dissolved in the solvent at a certain temperature and at a certain weight concentration of 1,4-bis(4-phenoxybenzoyl)benzene and if the corresponding temperature/concentration point is situated above the curve, then the 1,4-bis(4-phenoxybenzoyl)benzene-Lewis acid complex is in the supersaturated state.

It has been found by the present inventors that maintaining the 1,4-bis(4-phenoxybenzoyl)benzene-Lewis acid complex in a supersaturated state during part of the reaction step can result in an increased yield or conversion.

Figure 2:
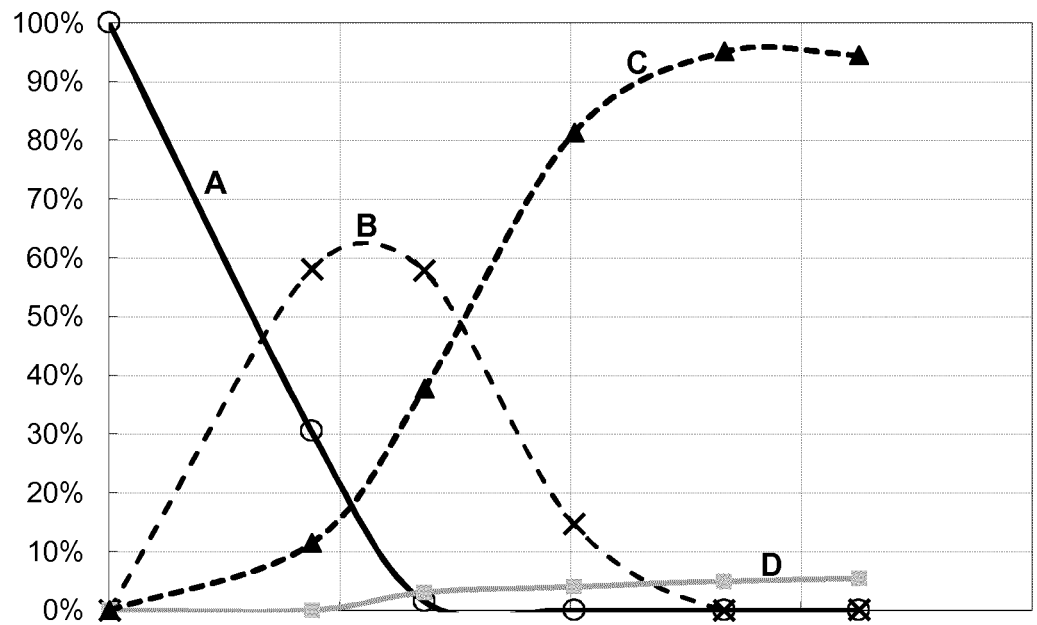
FIG. 2 schematically shows the evolution of the concentration of terephthaloyl chloride (A), 4-(4-phenoxybenzoyl)benzoyl chloride (as defined below) (B), 4-bis(4-phenoxybenzoyl)benzene (C) and xanthydrol moiety-containing molecules (D) as a function of the progression of the reaction. The concentrations are provided in mol. % relative to the initial total amount of terephthaloyl chloride. The progression of the reaction is indicated in arbitrary units on the X-axis.

The phenomenon at stake is schematically illustrated in FIG. 2, which shows the typical evolution of the concentration of the relevant species in the reactant mixture during the reaction step. It can be seen that, as terephthaloyl chloride (A) is consumed, the 4-(4-phenoxybenzoyl)benzoyl chloride (B) is initially produced in a large amount. Then the concentration of 4-(4-phenoxybenzoyl)benzoyl chloride in the reactant mixture reaches a peak and decreases, while the concentration of the desired product (C) increases. The amount of xanthydrol moiety-containing impurities (D) increases over time but remains at a relatively low level.

If the 1,4-bis(4-phenoxybenzoyl)benzene-Lewis acid complex precipitates during the reaction step, it is believed (without wishing to be bound by any theory) that part of the unreacted 4-(4-phenoxybenzoyl)benzoyl chloride is caught in the precipitate and thus substantially prevented from further reacting. In other terms, after the 1,4-bis(4-phenoxybenzoyl)benzene-Lewis acid complex has precipitated, it is believed that the conversion of the remaining 4-(4-phenoxybenzoyl)benzoyl chloride (B) to the desired product (C) is significantly impeded.

Therefore, in preferred embodiments, this precipitation is either prevented or at least postponed during the reaction step, without however keeping the concentration of 1,4-bis(4-phenoxybenzoyl)benzene-Lewis acid complex in the mixture at a low level, which would in turn reduce the overall efficiency and kinetics of the reaction. This is made possible because the 1,4-bis(4-phenoxybenzoyl)benzene-Lewis acid complex remains dissolved in the solvent during at least part of the reaction step even after its concentration has reached the saturation limit.

According to some variations, the 1,4-bis(4-phenoxybenzoyl)benzene-Lewis acid complex precipitates at some point of time during the reaction step (after the concentration of this species has exceeded the saturation limit).

According to alternative variations, the 1,4-bis(4-phenoxybenzoyl)benzene-Lewis acid complex does not precipitate during the reaction step and remains dissolved in the solvent during the entirety of the reaction step.

Preferably, the 1,4-bis(4-phenoxybenzoyl)benzene-Lewis acid complex is dissolved in the solvent during at least 75%, or at least 80%, or at least 85%, or at least 90%, or at least 95%, or at least 98%, or at least 99% of the overall duration of the reaction step.

Preferably, the 1,4-bis(4-phenoxybenzoyl)benzene-Lewis acid complex is still dissolved in the solvent (i.e., has not precipitated), when it is present in an amount of 75 mol. %, (or in other variations 80 mol. %, or 85 mol. %, or 90 mol. %, or 91 mol. %, or 92 mol. %, or 93 mol. %, or 94 mol. %, or 95 mol. %) in the reactant mixture, said amount being expressed as the amount of 1,4-bis(4-phenoxybenzoyl)benzene relative to the initial amount of terephthaloyl chloride reactant which was introduced.

Preferably, the 1,4-bis(4-phenoxybenzoyl)benzene-Lewis acid complex is dissolved in the solvent at a 1,4-bis(4-phenoxybenzoyl)benzene weight concentration which is higher by at least 5%, (or in other variations by at least 10%, or 15%, or 20%, or 25%, or 30%, or 35%, or 40%) than the saturation limit of the 1,4-bis(4-phenoxybenzoyl)benzene-Lewis acid complex, during part of the reaction step, and for instance during at least 5 minutes, or at least 10 minutes, or at least 15 minutes, or at least 20 minutes, or at least 30 minutes, or at least 40 minutes, or at least 1 hour.

Preferably, the 1,4-bis(4-phenoxybenzoyl)benzene-Lewis acid complex is dissolved in the solvent (without precipitation) at a 1,4-bis(4-phenoxybenzoyl)benzene concentration of more than 5 wt. %, or more than 10 wt. %, or more than 15 wt. %, or more than 20 wt. %, or more than 25 wt. %, or more than 30 wt. %, or more than 35 wt. %, or more than 40 wt. %, or more than 50 wt. %, during part of the reaction step.

In order to maintain the concentration of dissolved 1,4-bis(4-phenoxybenzoyl)benzene-Lewis acid complex in the solvent above the saturation limit, nucleation of the precipitate should be prevented or at least delayed. Several measures can be taken in this respect, in a non-limiting manner, in addition to the quality of the starting materials (already addressed above).

First, the internal walls of the reactor (which are in contact with the reactant mixture) should have a low surface roughness. Preferably the surface roughness Ra (as defined in ISO 4287) of the walls should be less than 2 μm, or less than 1 μm, or less than 0.8 μm, or less than 0.5 μm, or less than 0.2 μm.

Similarly, it is preferable that all equipment surfaces in contact with the reactant mixture during the reaction step, such as the surfaces of an impeller (if any) or the internal surfaces of a recirculation loop, should also have a rugosity of less than 2 μm, or less than 1 μm, or less than 0.8 μm, or less than 0.5 μm, or less than 0.2 μm.

Second, the method may comprise a preliminary step of washing the reactor, in order to eliminate all solid residues, such as dust particles or residual product particles from a previous reaction, before providing the reactant mixture in the reactor. As an example, this can be achieved by spraying or blasting a liquid or a solid or a suspension on reactor wall, preferably the reaction solvent, or by filling the reactor with a liquid or a suspension under agitation, or by any mechanical action.

Third, the method may comprise a step of eliminating solid particles from the reactant mixture, either before the start of the reaction step or during the reaction step, such as by filtration (including, e.g., ultrafiltration).

Fourth, the conditions (in particular intensity) of agitation during the reaction step may be selected in such a manner that the average shear stress (calculated as the product $K_{mo} \times N$ where $K_{mo}$ is the Metzner-Otto constant for the impellers used and N is the rotation frequency) for the reactant mixture remains below 100 $s^{-1}$, preferably below 50 $s^{-1}$, more preferably below 25 $s^{-1}$, even more preferably below 20 $s^{-1}$ during at least part of the reaction step, and more particularly during the part of the reaction step when the concentration of the dissolved 1,4-bis(4-phenoxybenzoyl)benzene-Lewis acid complex in the solvent is above the saturation limit (such as during the last 5%, or the last 10%, or the last 15%, or the last 20%, or the last 25%, or the last 30%, or the last 35%, or the last 40%, or the last 45%, or the last 50% of the reaction step, relative to the overall duration of the reaction step).

The reaction at stake is exothermic. Preferably, a temperature control system is provided, in order to control the temperature of the reactant mixture in the reactor, in particular during and after addition of the Lewis acid. The temperature control system may in particular comprise a temperature sensor within the reactor and may be configured to cool and/or to heat the reactant mixture. Preferably, it is at least configured to cool the reactant mixture.

Devices for heating and/or cooling the reactant mixture may include a heat exchanger inside the reactor or in a recirculation loop, or a heat exchange fluid circuit in the jacket of the reactor.

When the temperature of the reactant mixture increases during the step of adding the Lewis acid, this can be achieved in three different manners:
- by heating the reactant mixture (while preferably also controlling the rate of addition of the Lewis acid, so as to achieve a targeted increase in temperature);
- by simply controlling the rate of addition of the Lewis acid so as to achieve a targeted increase in temperature, without providing external cooling or heating;
or
- by cooling the reactant mixture, while also controlling the rate of addition of the Lewis acid, so as to achieve a targeted increase in temperature According to a preferred embodiment, the reactant mixture is cooled during and possibly also after the step of adding the Lewis acid, in order to prevent an excessively large or rapid increase in temperature of the reactant mixture as the reactants start reacting with each other.

Preferably, the temperature of the reactant mixture is greater than 5° C. during at least part of the step of adding the Lewis acid to the reactant mixture. In particular variations of the invention, the temperature of the reactant mixture is at least 10° C., or at least 15° C., or at least 20° C., or at least 25° C., or at least 30° C., or at least 35° C., or at least 40° C., or at least 45° C., or at least 50° C., or at least 55° C., or at least 60° C., during at least part of the step of adding the Lewis acid to the reactant mixture.

It should be noted that, when the temperature is higher, the saturation limit of the 1,4-bis(4-phenoxybenzoyl)benzene-Lewis acid complex is also higher, so that a relatively high temperature during at least part of the reaction step is useful for preventing or delaying the undesired precipitation of the 1,4-bis(4-phenoxybenzoyl)benzene-Lewis acid complex.

Besides, it has surprisingly been found that conducting the reaction step at a relatively high temperature, results in an increase in the yield of 1,4-bis(4-phenoxybenzoyl)benzene, without any significant increase in the level of by-product impurities such as xanthydrol moiety-containing molecules.

On the other hand, the temperature during the step of adding the Lewis acid to the reactant mixture should preferably remain below a certain threshold in order to avoid any significant polymerization of the reactants into a PEKK polymer.

Furthermore, the temperature during the step of adding the Lewis acid to the reactant mixture should remain below the boiling temperature of the solvent.

It is possible to operate the reactor in a pressurized manner so that the temperature in the reactor can reach a higher value without causing the solvent to boil. In this case, the pressure in the reactor can range from 1 bar (atmospheric pressure) to 6 bar, preferably from 1.5 bar to 3 bar.

Alternatively, and preferably, the reaction is performed at atmospheric pressure.

According to some variants of the invention, the temperature of the reactant mixture does not exceed 100° C., preferably 90° C., more preferably 80° C., even more preferably 70° C., during the step of adding the Lewis acid.

It is believed that it is more critical for the temperature of the reactant mixture to be relatively high at the end of the step of adding the Lewis acid than at the beginning of this step, in order to achieve the advantageous effects of the invention.

Accordingly, in some variants of the invention, once 90% by weight of Lewis acid has been added to the reactant mixture (relative to the total weight of Lewis acid added to the reactant mixture), it is preferred that the temperature of the reactant mixture is and remains of at least 5° C., preferably at least 10° C., or at least 15° C., or at least 20° C., or at least 25° C., or at least 30° C., or at least 35° C., or at least 40° C., or at least 45° C., or at least 50° C., or at least 55° C., or at least 60° C., during the remainder of the step of adding the Lewis acid to the reactant mixture.

In some variants of the invention, once 75% by weight of Lewis acid has been added to the reactant mixture (relative to the total weight of Lewis acid added to the reactant mixture), it is preferred that the temperature of the reactant mixture is and remains of at least 5° C., preferably at least 10° C., or at least 15° C., or at least 20° C., or at least 25° C., or at least 30° C., or at least 35° C., or at least 40° C., or at least 45° C., or at least 50° C., or at least 55° C., or at least 60° C., during the remainder of the step of adding the Lewis acid to the reactant mixture.

In some variants of the invention, once 50% by weight of Lewis acid has been added to the reactant mixture (relative to the total weight of Lewis acid added to the reactant mixture), it is preferred that the temperature of the reactant mixture is and remains of at least 5° C., preferably at least 10° C., or at least 15° C., or at least 20° C., or at least 25° C., or at least 30° C., or at least 35° C., or at least 40° C., or at least 45° C., or at least 50° C., or at least 55° C., or at least 60° C., during the remainder of the step of adding the Lewis acid to the reactant mixture.

In some variants of the invention, once 20% by weight of Lewis acid has been added to the reactant mixture (relative to the total weight of Lewis acid added to the reactant mixture), it is preferred that the temperature of the reactant mixture is and remains of at least 5° C., preferably at least 10° C., or at least 15° C., or at least 20° C., or at least 25° C., or at least 30° C., or at least 35° C., or at least 40° C., or at least 45° C., or at least 50° C., or at least 55° C., or at least 60° C., during the remainder of the step of adding the Lewis acid to the reactant mixture.

The temperature of the reactant mixture can remain constant during the step of adding the Lewis acid. Alternatively, it can vary during this step.

By "initial temperature" is meant the temperature of the reactant mixture at the beginning of the step of adding the Lewis acid, i.e., as the first molecules of Lewis acid are added to the reactant mixture.

By "final temperature" is meant the temperature of the reactant mixture at the end of the step of adding the Lewis acid, i.e., as the last molecules of Lewis acid are added to the reactant mixture.

The initial temperature of the reactant mixture may range from, e.g., −30° C. to 80° C. In some variations, the initial temperature of the reactant mixture is from −30 to −25° C.; or from −25 to −20° C.; or from −20 to −15° C.; or from −15 to −10° C.; or from −10 to −5° C.; or from −5 to −0° C.; or from 0 to 5° C.; or from 5 to 10° C.; or from 10 to 15° C.; or from 15 to 20° C.; or from 20 to 25° C.; or from 25 to 30° C.; or from 30 to 35° C.; or from 35 to 40° C.; or from 40 to 45° C.; or from 45 to 50° C.; or from 50 to 55° C.; or from 55 to 60° C.; or from 60 to 65° C.; or from 65 to 70° C.; or from 70 to 75° C.; or from 75 to 80° C. Ranges of from 0 to 80° C., more particularly from 20 to 50° C. are preferred.

The final temperature of the reactant mixture may range from, e.g., 10° C. to 80° C. In some variations, the final temperature of the reactant mixture is from 10 to 15° C.; or from 15 to 20° C.; or from 20 to 25° C.; or from 25 to 30° C.; or from 30 to 35° C.; or from 35 to 40° C.; or from 40 to 45° C.; or from 45 to 50° C.; or from 50 to 55° C.; or from 55 to 60° C.; or from 60 to 65° C.; or from 65 to 70° C.; or from 70 to 75° C.; or from 75 to 80° C. Ranges of from 30 to 80° C., and more particularly from 40 to 70° C., even more particularly from 45 to 60° C. are preferred. In some variations, the final temperature is at least 30° C., preferably at least 40° C., more preferably at least 45° C. and most preferably at least 50° C.

In some variations, the temperature of the reactant mixture decreases during the step of adding the Lewis acid, i.e., the final temperature is lower than the initial temperature.

In preferred variations, the temperature of the reactant mixture increases during the step of adding the Lewis acid, i.e., the final temperature is greater than the initial temperature.

In some embodiments, the temperature difference ΔT between the final temperature and the initial temperature is from 5 to 60° C., preferably from 10 to 50° C., more preferably from 20 to 40° C.

In some variations of the invention, the increase in temperature is monotonous, i.e., there is no transient decrease in temperature during the entire step of adding the Lewis acid. On the other hand, transient variations or fluctuations in temperature are possible in some embodiments, especially due to the non-instantaneous nature of the temperature control.

In some variations, the temperature of the reactant mixture continuously increases from the initial temperature to the final temperature. Alternatively, the temperature of the reactant mixture may comprise one or more increase stages and one more plateau stages during the step of adding the Lewis acid. In particular, the temperature of the reactant mixture may initially increase during a first part of the step of adding the Lewis acid, from the initial temperature to the final temperature, and then plateau at the final temperature during a second part of the step of adding the Lewis acid. In this case, the plateau temperature may be set with a precision of, e.g., +/−5° C., or +/−2° C., or +/−1° C.

There is no limitation as to the temperature of the reactant mixture during the optional step of maintaining the reactant mixture, after the addition of the Lewis acid. In some variations of the invention, the temperature of the mixture is maintained at the final temperature described above. In other variations, it increases or decreases relative to the final temperature.

The method of the invention may advantageously comprise one or more steps (after the reaction step) for purifying 1,4-bis(4-phenoxybenzoyl)benzene from the product mixture, and in particular from the solvent, catalyst and unreacted reactants as well as by-products. The purification may comprise the steps of:
    mixing the product mixture with a protic solvent so as to provide a product slurry;

separating 1,4-bis(4-phenoxybenzoyl)benzene from the product slurry, preferably by filtration and washing.

The protic solvent used to make the product slurry is advantageously selected so that 1,4-bis(4-phenoxybenzoyl)benzene tends to easily precipitate. By way of example, methanol may be used as a protic solvent.

The protic solvent can be an organic solvent, such as methanol, acetic acid, formic acid, ethanol, isopropanol, and benzyl alcohol.

Alternatively, the protic solvent can be an aqueous solution.

Mixtures of the above solvents can also be used, such as an aqueous-organic solvent, e.g., an aqueous solution mixed with methanol.

The desired product can then be recovered from the product slurry by filtration. If necessary, the product can be washed, preferably by a protic solvent such as methanol, and filtrated again, once or several times. Washing can be performed for example by re-slurrying the product in the solvent.

The 1,4-bis(4-phenoxybenzoyl)benzene obtained according to the invention can subsequently be used to perform a polymerization reaction so as to make a PEKK polymer.

In order to make the PEKK polymer, 1,4-bis(4-phenoxybenzoyl)benzene is reacted with at least one difunctional aromatic acyl chloride.

The difunctional aromatic acyl chloride may in particular include terephthaloyl chloride, isophthaloyl chloride and more preferably a mixture of terephthaloyl chloride and isophthaloyl chloride.

The reaction is preferably implemented in a solvent. The solvent is preferably a non-protic solvent, which can in particular be selected from methylene chloride, carbon disulfide, ortho-dichlorobenzene, meta-dichlorobenzene, para-dichlorobenzene, 1,2,4-trichlorobenzene, 1,2,3-trichlorobenzene, ortho-difluorobenzene, 1,2-dichloroethane, 1,1,2,2-tetrachloroethane, tetrachloroethylene, dichloromethane, nitrobenzene and mixtures thereof.

The reaction is preferably implemented in the presence of a Lewis acid as a catalyst.

Lewis acids which may be used include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. Aluminum trichloride, boron trichloride, aluminum tribromide, titanium tetrachloride, antimony pentachloride, ferric chloride, gallium trichloride, and molybdenum pentachloride are preferred. Aluminum trichloride is particularly preferred.

The polymerization can be implemented in the same reactor as the one used for the production of 1,4-bis(4-phenoxybenzoyl)benzene. But more preferably it is implemented in one or more other reactors.

The polymerization can be carried out at a temperature ranging from, e.g., 50 to 120° C.

The method of making the PEKK polymer advantageously also comprises one or more steps for purifying the PEKK polymer, such as steps of:
  mixing the mixture containing the PEKK polymer with a protic solvent so as to provide a PEKK slurry;
  separating the PEKK polymer from the PEKK slurry, preferably by filtration and washing.

The protic solvent used to make the PEKK slurry may be, e.g., methanol.

The PEKK polymer can then be recovered from the PEKK slurry by filtration. If necessary, the polymer can be washed, preferably by a protic solvent such as methanol, and filtrated again, once or several times. Washing can be performed for example by re-slurrying the polymer in the solvent.

EXAMPLES

The following examples illustrate the invention without limiting it.

Example 1

Terephthaloyl chloride yielding a very clear solution when dissolved at 6.5 wt. % in ortho-dichlorobenzene (turbidity of less than 10 NTU) was used as a starting material.

In a 2 L reactor equipped with a mechanical stirrer, with a nitrogen inlet and an outlet going to a scrubber system, 745 g of ortho-dichlorobenzene, 82 g of terephthaloyl chloride and 206 g of diphenyl ether were introduced.

After full solubilization, the mixture was heated up to 35° C. While keeping the temperature at 35° C., 175 g of $AlCl_3$ were slowly added to the reactant mixture. After completion of $AlCl_3$ addition, the mixture was kept agitated at 35° C. for 1 hour to finish the reaction.

The relative molar composition of the desired product, by-products and unconverted terephthaloyl chloride (in the esterified form of dimethyl terephthalate) was calculated from NMR analysis of the organic mixture obtained after synthesis, based on the characteristic peaks of the relevant species.

Example 2

An experiment similar to example 1 was conducted, except that terephthaloyl chloride yielding a cloudy suspension when dissolved at 6.5 wt. % in ortho-dichlorobenzene (turbidity of more than 100 NTU) was used as a starting material. The obtained product was characterized in the same manner as in Example 1.

The results of examples 1 and 2 are summarized in the table below:

|  | Example No. | |
| --- | --- | --- |
|  | 1 | 2 |
| Mol. % dimethyl terephthalate | 0 | 0 |
| Mol. % 1,4-bis(4-phenoxybenzoyl)benzene | 95.6 | 91.2 |
| Mol. % 4-(4-phenoxybenzoyl)benzoic acid methyl-ester + 4-(4-phenoxybenzoyl)benzoic acid | 0.1 | 5.4 |
| Mol. % xanthydrol moiety-containing molecules | 4.3 | 3.4 |

Examples 3-4

In a 2 L reactor equipped with a mechanical stirrer, with a nitrogen inlet and an outlet going to a scrubber system, 745 g of ortho-dichlorobenzene were introduced. Then 39 g of terephthaloyl chloride and 97 g of diphenyl ether were introduced.

After full solubilization, the mixture was cooled down to 0° C. While keeping the temperature at 0° C., 83 g of $AlCl_3$ were slowly added to the reactant mixture. After completion of $AlCl_3$ addition, the mixture was kept agitated at 0° C. during 20 min to finish the reaction.

After subsequent workup, the purity of the resulting product was measured by HPLC.

Examples 5-7

In a 2 L reactor equipped with a mechanical stirrer, with a nitrogen inlet and an outlet going to a scrubber system, 745 g of ortho-dichlorobenzene were introduced. The solvent was heated up to 130° C. and the first vapor containing the azeotrope water/ortho-dichlorobenzene was removed from the system. It was then cooled down to room temperature. Then 39 g of terephthaloyl chloride and 97 g of diphenyl ether were introduced.

After full solubilization, the mixture was cooled down to 0° C. While keeping the temperature at 0° C., 83 g of $AlCl_3$ were slowly added to the reactant mixture. After completion of $AlCl_3$ addition, the mixture was kept agitated at 0° C. during 20 min to finish the reaction.

After subsequent workup, the purity of the resulting product was measured by HPLC.

The results of examples 3 to 7 are summarized in the table below:

|  | Example No. | | | | |
| --- | --- | --- | --- | --- | --- |
|  | 3 | 4 | 5 | 6 | 7 |
| Solvent dehydration | no | no | Yes | yes | Yes |
| Purity (wt. %) | 99.38 | 98.78 | 99.52 | 99.74 | 99.78 |

The invention claimed is:

1. A method for manufacturing 1,4-bis(4-phenoxybenzoyl)benzene, comprising:
providing terephthaloyl chloride, diphenyl ether, a solvent and a Lewis acid, wherein the terephthaloyl chloride is of a purity grade such that, 10 minutes after introducing it at a reference concentration of 6.5 wt. % into said solvent, at a temperature of 20° C., a solution is obtained having a turbidity of less than 500 NTU;
reacting terephthaloyl chloride with diphenyl ether in the solvent and in the presence of the Lewis acid; and
recovering a product mixture comprising a 1,4-bis(4-phenoxybenzoyl)benzene-Lewis acid complex.

2. The method of claim 1, wherein the terephthaloyl chloride is of a purity grade such that:
10 minutes after introducing it at a reference concentration of 6.5 wt. % into said solvent, at a temperature of 20° C., a solution is obtained having a turbidity of less than 200 NTU.

3. The method of claim 1, reacting terephthaloyl chloride with diphenyl ether in the solvent and in the presence of the Lewis acid comprises:
mixing the terephthaloyl chloride, the diphenyl ether and the solvent so as to make a reactant mixture; and
adding the Lewis acid to the reactant mixture so as to effect the reaction of the terephthaloyl chloride with the diphenyl ether.

4. The method of claim 3, wherein the terephthaloyl chloride is kept in a sealed container without contact with ambient air prior to making the reactant mixture.

5. The method of claim 1, wherein the diphenyl ether and solvent, in combination, contain less than 500 ppm by weight of water.

6. The method of claim 1, wherein the diphenyl ether and solvent, in combination, contain from 1 to 250 ppm by weight of water.

7. The method of claim 3, comprising a step of drying the solvent or of drying the solvent combined with the diphenyl ether prior to adding the terephthaloyl chloride to the solvent.

8. The method of claim 1, wherein the 1,4-bis(4-phenoxybenzoyl)benzene-Lewis acid complex is dissolved in the solvent at a 1,4-bis(4-phenoxybenzoyl)benzene weight concentration in the solvent which is higher than the saturation limit of the 1,4-bis(4-phenoxybenzoyl)benzene-Lewis acid complex during at least part of the reaction of the terephthaloyl chloride with the diphenyl ether.

9. The method of claim 1, wherein the 1,4-bis(4-phenoxybenzoyl)benzene-Lewis acid complex is dissolved in the solvent at a 1,4-bis(4-phenoxybenzoyl)benzene weight concentration which is higher by at least 5% than the saturation limit of the 1,4-bis(4-phenoxybenzoyl)benzene-Lewis acid complex, during part of the reaction of the terephthaloyl chloride with the diphenyl ether.

10. The method of claim 1, wherein the 1,4-bis(4-phenoxybenzoyl)benzene-Lewis acid complex is dissolved in the solvent at a 1,4-bis(4-phenoxybenzoyl)benzene weight concentration of more than 5 wt. %, during part of the reaction of the terephthaloyl chloride with the diphenyl ether.

11. The method of claim 1, wherein the 1,4-bis(4-phenoxybenzoyl)benzene-Lewis acid complex is dissolved in the solvent during at least 75% of the duration of the reaction of the terephthaloyl chloride with the diphenyl ether.

12. The method of claim 3 wherein the 1,4-bis(4-phenoxybenzoyl)benzene-Lewis acid complex is dissolved in the solvent when an amount of 1,4-bis(4-phenoxybenzoyl)benzene of 75 mol. %, relative to the initial amount of terephthaloyl chloride, is present in the reactant mixture.

13. The method of claim 1, wherein the Lewis acid is aluminum trichloride.

14. The method of claim 1, wherein the solvent is ortho-dichlorobenzene.

15. The method of claim 1, comprising the additional steps of:
mixing the product mixture with a protic solvent so as to provide a product slurry;
separating 1,4-bis(4-phenoxybenzoyl)benzene from the product slurry.

16. A method of making a polyether ketone ketone polymer, comprising:
manufacturing 1,4-bis(4-phenoxybenzoyl)benzene according to the method of claim 1;
reacting said 1,4-bis(4-phenoxybenzoyl)benzene with at least one difunctional aromatic acyl chloride.

* * * * *